(12) United States Patent
Lockhart et al.

(10) Patent No.: US 7,477,925 B2
(45) Date of Patent: Jan. 13, 2009

(54) ERYTHEMA MEASURING DEVICE AND METHOD

(75) Inventors: Peter B. Lockhart, Charlotte, NC (US); Robert Splinter, Huntersville, NC (US); Michael T. Brennan, Charlotte, NC (US); Philip C. Fox, Cabin John, MD (US)

(73) Assignee: Charlotte-Mecklenburg Hospital Authority, Charlotte, NC (US)

( * ) Notice: Subject to any disclaimer, the term of this patent is extended or adjusted under 35 U.S.C. 154(b) by 720 days.

(21) Appl. No.: 10/681,722

(22) Filed: Oct. 8, 2003

(65) Prior Publication Data

US 2004/0073374 A1    Apr. 15, 2004

Related U.S. Application Data

(63) Continuation-in-part of application No. 10/053,103, filed on Jan. 17, 2002, now Pat. No. 6,862,542.

(51) Int. Cl.
*A61B 5/05* (2006.01)
*A61B 8/00* (2006.01)
*A61B 8/12* (2006.01)
*A61B 8/14* (2006.01)

(52) U.S. Cl. .................. 600/407; 600/427; 600/437; 600/438; 600/442; 600/340; 600/473; 600/475; 600/478; 606/2.5; 433/29; 433/72

(58) Field of Classification Search ............. 600/407, 600/437, 438, 427, 442, 340, 473, 475, 478; 702/19, 76; 205/339.01, 339.02, 341.1, 341.2, 205/341.3; 433/29, 73; 606/2.5
See application file for complete search history.

(56) References Cited

U.S. PATENT DOCUMENTS

| | | | | |
|---|---|---|---|---|
| 4,836,206 A | * | 6/1989 | Maxwell et al. | 600/340 |
| 5,040,539 A | * | 8/1991 | Schmitt et al. | 600/340 |
| 5,109,859 A | * | 5/1992 | Jenkins | 600/439 |
| 5,202,939 A | * | 4/1993 | Belleville et al. | 385/12 |
| 5,749,364 A | * | 5/1998 | Sliwa et al. | 600/438 |
| 5,873,875 A | * | 2/1999 | Altshuler | 606/10 |
| 6,436,127 B1 | * | 8/2002 | Anderson et al. | 607/89 |
| 6,546,272 B1 | * | 4/2003 | MacKinnon et al. | 600/407 |
| 6,584,341 B1 | * | 6/2003 | Mandelis et al. | 600/476 |
| 2001/0018554 A1 | * | 8/2001 | Yamashita et al. | 600/178 |
| 2002/0026127 A1 | * | 2/2002 | Balbierz et al. | 600/567 |

\* cited by examiner

*Primary Examiner*—Ruth S Smith
*Assistant Examiner*—James Kish
(74) *Attorney, Agent, or Firm*—George R. McGuire; David L. Nocilly; Bond Schoeneck & King, PLLC

(57) ABSTRACT

An erythema meter includes a probe, a light source of one or more specific probing and reference wavelengths, and an acoustic detector which determines the level of erythema present in the dental pulp chamber of a tooth. The probing and reference wavelengths are delivered in pulsed or amplitude modulated fashion through the probe, thereby permitting electronic identification and filtering of the received data. The absorption of the light wave raises the temperature of the material in the tooth and causes it to expand, thus creating tiny shockwaves which are picked up with the acoustic detector, revealing information on the location of blood and the quantity of blood inside the tooth. The erythema meter accurately measures the erythema, or inflammation, within the tooth in a qualitative and quantitative manner.

45 Claims, 2 Drawing Sheets

ERYTHEMA MEASURING DEVICE AND METHOD

CROSS-REFERENCE TO RELATED APPLICATIONS

This application is a continuation-in-part of U.S. application Ser. No. 10/053,103 filed Jan. 17, 2002, now U.S. Pat. No. 6,862,542 incorporated herein by reference.

FIELD OF THE INVENTION

This invention relates generally to the field of devices for detecting the health status of the pulp tissue within a tooth, and more particularly to a device and method for using a combination of light and acoustics to measure the degree of erythema in a tooth.

BACKGROUND OF THE INVENTION

Erythema refers to redness, or inflammation of vascularized areas of the body, which can increase as a result of various causes including diseases and disorders of the mucosa and skin, and of the dental pulp ("tooth nerve") tissue. There is a long-standing problem of determining the health status of the contents of the dental pulp chamber within teeth. The pulp consists of different tissues, including a dense network of small blood vessels. In the healthy state, the pulp tissue is red in color due to a rich blood supply. When a tooth becomes diseased from caries (decay), or injured from trauma, the dental pulp becomes inflamed, and in the case of caries, the degree of erythema might increase, first near the area of disease (caries) in the crown portion of the tooth, and ultimately progressing throughout the pulp chamber and root canal(s) to the apex of the tooth, where the pulp tissue joins the systemic circulation in the surrounding alveolar bone. This increased erythema eventually disappears as the pulp becomes overwhelmed by the inflammatory process, loses its blood supply, and becomes necrotic. This can be painful, but in many cases it is a silent process. The resulting infection can ultimately spread to the soft tissues of the face, involving vital structures of the head and neck, and on rare occasions can result in death.

Methods to determine the health status of the dental pulp are crude, often highly subjective, and have not progressed significantly in the last three decades. Part of the problem stems from the two different layers of calcified tissue, dentin and enamel, that surround the pulp tissue. The standard method for visualizing the dental pulp is to use the intraoral dental radiograph, which only gives a two-dimensional view, or shadow, of the pulp chamber. Radiographs do not allow for differentiation between the extremes of entirely healthy versus completely necrotic pulp tissue.

The determination of the degree of erythema, and therefore the degree of disease of pulp tissue, has always been of interest to dentists in clinical practice and in research, as it would allow for early diagnosis, less invasive treatment, and less costly treatment. It would also allow for the development of medications to prevent or treat pulpal inflammation. This would provide for early intervention in situations where the inflammatory process could be altered, and provide a research tool for studies concerning disorders where tooth vascularity may be altered by changes in the blood supply. There are no practical or commercial methods for quantifying erythema within teeth, and existing methods of determining the health status of the pulp are highly subjective, poorly reproducible, and often do not detect disease at an early stage when treatment and preventative strategies are most effective.

SUMMARY OF THE INVENTION

Briefly stated, an erythema meter includes a probe, a light source of one or more specific probing and reference wavelengths, and an acoustic detector which determines the level of erythema present in the dental pulp chamber of a tooth. The probing and reference wavelengths are delivered in pulsed or amplitude modulated fashion through the probe, thereby permitting electronic identification and filtering of the received data. The absorption of the light wave raises the temperature of the material in the tooth and causes it to expand, thus creating tiny shockwaves which are picked up with the acoustic detector, revealing information on the location of blood and the quantity of blood inside the tooth. The erythema meter accurately measures the erythema, or inflammation, within the tooth in a qualitative and quantitative manner.

According to an embodiment of the invention, a system for measuring erythema in a tooth includes means for generating light of a first frequency; means for transmitting the light of the first frequency into the tooth; means for detecting shock waves induced in the tooth by the transmitted light of the first frequency; and means for processing the detected shock waves induced by the transmitted light of the first frequency to measure the erythema in the tooth.

According to a feature of the invention, the system further includes means for generating light of a second frequency; means for modulating the light of the first frequency; means for modulating the light of the second frequency, wherein the modulation of the second frequency is different from the modulation of the first frequency; the means for transmitting the light of the first frequency into the tooth being effective for transmitting the light of the second frequency into the tooth; the means for detecting shock waves induced in the tooth by the transmitted light of the first frequency being effective for detecting shock waves induced in the tooth by the transmitted light of the second frequency; and the means for processing the detected shock waves induced by the transmitted light of the first frequency being effective for processing the detected shock waves induced in the tooth by the transmitted light of the second frequency to measure the erythema in the tooth.

According to an embodiment of the invention, a system for measuring erythema in a tooth includes a generator for generating light of a first frequency; a probe which transmits the light of the first frequency into the tooth; a detector which detects shock waves induced in the tooth by the transmitted light of the first frequency; and a processor which processes the detected shock waves induced by the transmitted light of the first frequency to measure the erythema in the tooth.

According to a feature of the invention, the system further includes a generator for generating light of a second frequency; a modulator for modulating the light of the first frequency; a modulator for modulating the light of the second frequency; wherein the probe transmits the modulated light of the first and second frequencies into the tooth; the detector detects shock waves induced in the tooth by the transmitted modulated light of the first and second frequencies; and the processor processes the detected shock waves induced by the transmitted modulated light of the first and second frequencies to measure the erythema in the tooth.

According to an embodiment of the invention, a method for measuring erythema in a tooth includes the steps of generating light of a first frequency; transmitting the light of the first frequency into the tooth; detecting shock waves induced in the tooth by the transmitted light of the first frequency; and processing the detected shock waves induced by the transmitted light of the first frequency to measure the erythema in the tooth.

According to a feature of the invention, the method further includes the steps of generating light of a second frequency; modulating the light of the first frequency; modulating the light of the second frequency, wherein the modulation of the second frequency is different from the modulation of the first frequency; transmitting the light of the first and second frequencies into the tooth; detecting shock waves induced in the tooth by the transmitted light of the first and second frequencies; and processing the detected shock waves induced by the transmitted light of the first and second frequencies to measure the erythema in the tooth.

DETAILED DESCRIPTION OF THE PREFERRED EMBODIMENT

Figure 1:
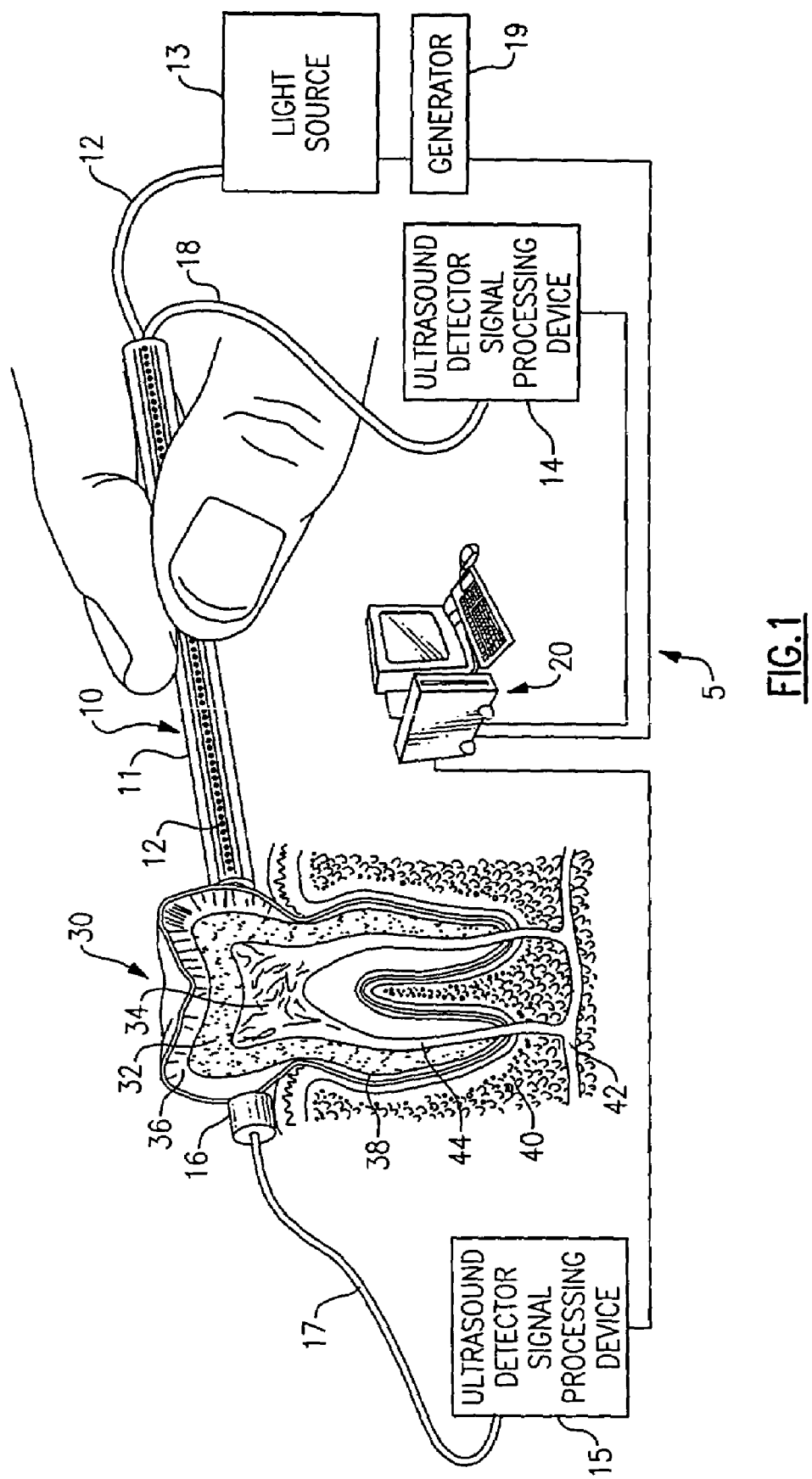
FIG. 1 shows a diagram of the delivery and detection protocol of the present invention, i.e., a system for measuring tooth erythema and for measuring the blood supply to the tooth.

Referring to FIG. 1, a tooth 30 is shown. A layer of dentin 32 protects an inner layer of pulp 34. Tooth 30 includes an outer protective layer of enamel 36 which protects that part of dentin 32 which is not protected by the gums. A layer of cementum 38 covers that part of dentin 32 which is protected by the gums. Tooth 30 is embedded in a layer of alveolar bone 40 in the mouth. The systemic circulation system has a portion 42 which interconnects with a root canal 44 inside tooth 30 to provide blood to pulp 34.

The degree to which the pulp in a tooth is healthy can be determined by knowing the state of its vascularity, or blood supply. The areas of interest are the root canal 44 and pulp 34 areas. These areas are screened from observation by enamel 36, cementum 38, and dentin 32, hereinafter referred to as the "opaque" areas. The method of the present invention is implemented by using frequencies of light which penetrate the opaque areas and interact with the media present in the areas of interest. The various media in the areas of interest preferably consist of blood, both oxygenated and deoxygenated, no blood, and infection. The wavelengths of the light are therefore selected so they pass through the opaque areas without too much interference and without causing unwanted side effects, such as cracking the tooth. The near infrared range of light is preferred, although the mid and far infrared ranges might also work. The visible wavelengths are to be avoided because there is too much scattering caused by the opaque areas. The preferred embodiment of the method of the present invention involves determining those frequencies of light which permit detection of (1) oxygenated blood, (2) deoxygenated blood, (3) no blood, and (4) infection. In addition, a frequency which doesn't react with any of the media present in the areas of interest is preferably used to detect the boundaries between the different areas of the tooth. Determination of the best frequencies to use for each of these purposes is believed to be possible through routine experimentation. The light frequencies need to penetrate 5-6 mm in tooth 30, and also preferably need to penetrate artificial crowns.

A detection and delivery system is shown generally at 5. A detector/probe 10 includes a light transmitting/carrying device, such as an optical fiber 12, and a sensor 11 which detects an acoustic shock wave. A generator 19 is electrically coupled to a light source 13 such as a laser or LED. Several light sources are preferable so that different wavelengths of light can be transmitted simultaneously through detector/probe 10, although a tunable light source would work with the different frequencies transmitted sequentially instead of simultaneously. Because sensor 11 has no way to determine which frequency of light activated the area of the tooth being studied, a unique identifier has to be imposed on each light frequency. In addition, a shock wave has to be induced in the area of interest by the light after the light penetrates the opaque areas. Both of these considerations are solved by modulating the light frequency with a pulse frequency, and using a different pulse frequency for each light frequency. The pulse frequency is preferably in the ultrasound range to take advantage of the known ultrasound imaging techniques which exist in the art. The pulse frequency also determines the resolution. Because blood vessels are on the order of microns, a range of 500 to 50,000 KHz should work for the pulse frequencies. The optimal pulse frequencies to use should be discoverable through routine experimentation. Amplitude modulation instead of pulse modulation of the light frequencies is also possible.

Generator 19 preferably houses at least two individual frequency generators for delivering a pulsed voltage to light source 13, which in turn delivers at least one light wave pulse train through optical fiber 12. As previously described, one of the light wavelengths preferably interacts with the blood content of the pulp to provide a measure of blood absorption, whether oxygenated or reduced. Alternately, a second wavelength in the spectral range of preferential absorption in blood may be used. An additional third wavelength light source may be chosen to determine the background, with no specific absorption difference between oxygenated or reduced blood, or dentin.

The qualitative and quantitative detection of blood inside tooth 30 is accomplished by delivery of femtosecond laser pulses in a repetition delivery protocol. The absorption of the light wave raises the temperature of the material and causes it to expand. As a consequence, a shock wave is created which can be detected by means of piezo-acoustic detectors such as sensor 11. Shockwave detection itself is known in art, being used in ultrasound imaging, for example. Fiber 12 inside probe 10 delivers the femtosecond light pulses to tooth 30. There are preferably two separate wavelengths from two separate pulsed lasers, one operating at a wavelength that penetrates enamel 36 and bone 40, while having greater than twice the absorption in Hb and/or $HbO_2$, thus creating sonic sources at the point of blood content. The wavelength of the laser light is varied to evaluate the best sensitivity point, which is the wavelength at which the blood and the surrounding media have the greatest difference in the absorption coefficient. A minimum of two separate wavelengths may be used to distinguish between oxygenated (HbO2) and deoxygenated (Hb) blood. Optionally, an additional third wavelength is at a wavelength range where Hb/HbO2 and other structures are overlapping in the absorption spectrum, thus providing a background check to be used for subtraction of the signal and contrast enhancement. Wavelengths are preferably selected based on their contrast in absorption with enamel and dentin, as well as various popular artificial dental crown materials, such as metals and alloys, ceramics, and combinations of these materials. The laser sources may have a variety of degrees of polarization, or be unpolarized, linearly polarized, or elliptically polarized. Fiber 12 maintains this state of polarization for additional discrimination potential of the delivery of the light to the target area inside tooth 30.

Generator 19 is preferably electrically connected to a calculating circuit or computer 20 via a standardized connection such as a parallel cable, RS232 cable, or USB cable. A wire 18 carries an electric signal generated in probe 10 by detector 11 to an ultrasound detector signal processing device 14. A second detector 16, or even a third detector (not shown), is optionally connected to a secondary ultrasound signal detection processing device 15 through a lead 17, to provide additional information on the location of sound wave generation. Thus, the shock waves generated by the absorption of these light pulses are detected with one or more detectors 11, 16 on either side of tooth 30, revealing three-dimensional information on the location of the absorption of laser pulses in blood as probe 10 is moved around different areas of tooth 30. Shock wave detectors 11, 16 can be any device that measures displacement, such as piezo-electric detectors or fiberoptic Fabry-Perot ultrasound sensor such as are known in the art. The pulsed wave of laser light is modulated with a frequency train, or by adding one extra pulse at specific intervals, thus providing a means to obtain time of travel and therefore information on depth. Structural detail can also be derived by analyzing the second harmonic of the ultrasound signal. The magnitude of the signal provides information on the amount of blood content. To be able to quantify the amount of blood present in the volume of observation and set criteria for normal or abnormal condition of the tooth pulp, data is processed preferably using image and pattern recognition techniques. These techniques allow the three dimensional picture of the volume to be reconstructed. In addition, the invention can be used to obtain images of healthy teeth for reference purposes, whether to compare the same tooth in a patient at regular intervals, or to obtain accepted data, stored in a database, on what healthy teeth should look like as obtained from measurements taken on a random group of test subjects.

Figure 2:
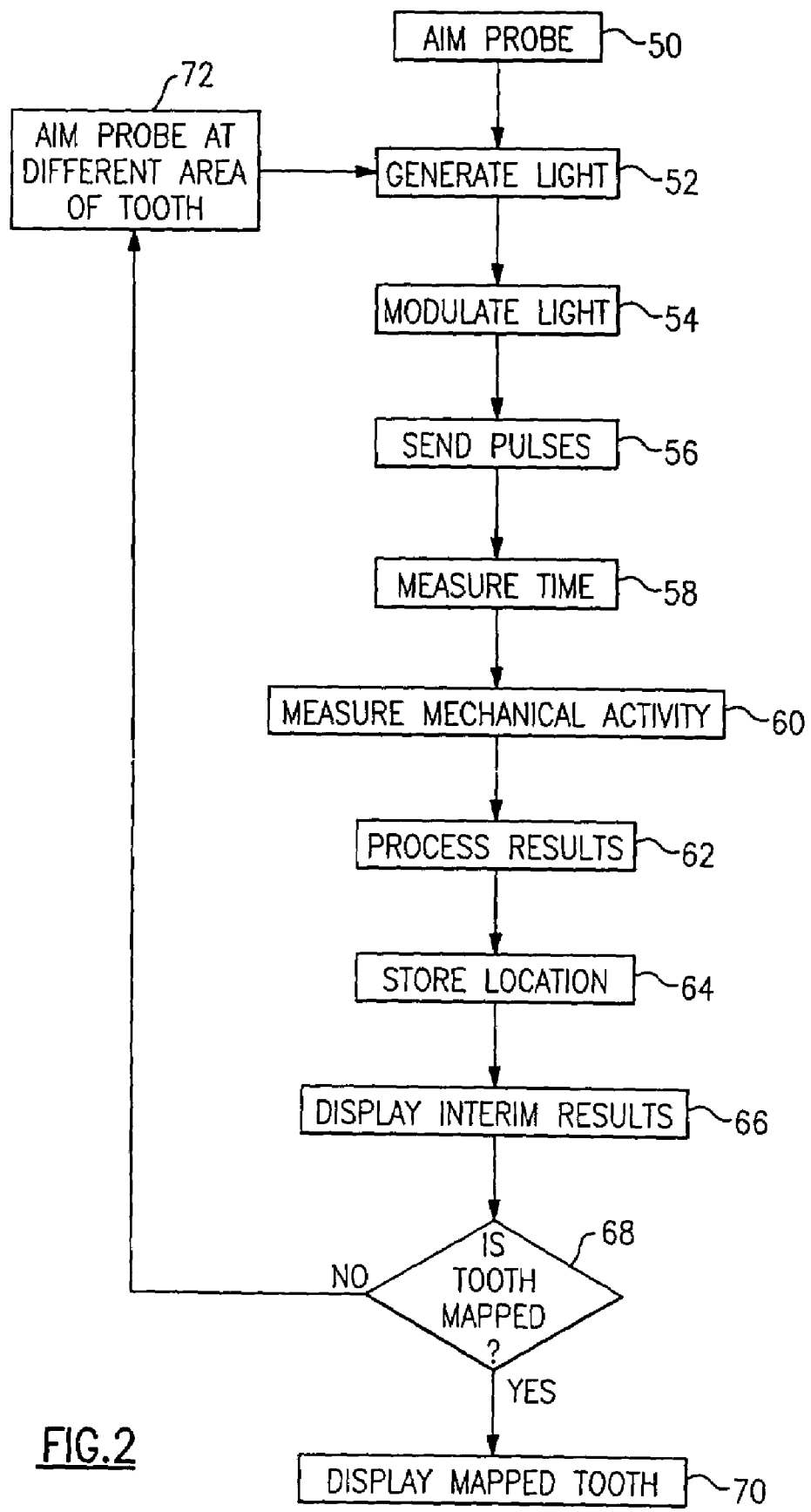
FIG. 2 shows a flow chart of a method of the present invention.

Referring to FIG. 2, a method according to an embodiment of the invention is shown. The probe is aimed at the tooth in step 50. Light of several frequencies is generated in step 52 and each frequency is modulated with a unique pulse frequency in step 54, after which the light pulses are sent in step 56. The time is measured in step 58 to obtain distance information. Mechanical activity of the tooth in response to the frequencies is measured in step 60. The results are processed in step 62, so that the determinations of oxygenated blood, deoxygenated blood, infection, no blood, and boundary area are made. The location(s) are stored in step 64, with the interim results preferably displayed in step 66. If the tooth is mapped in step 68, the mapped tooth is displayed in step 70. Otherwise, the probe is aimed at a different part of the tooth in step 72 and the process reverts to step 52.

While the present invention has been described with reference to a particular preferred embodiment and the accompanying drawings, it will be understood by those skilled in the art that the invention is not limited to the preferred embodiment and that various modifications and the like could be made thereto without departing from the scope of the invention as defined in the following claims.

What is claimed is:

1. A system for measuring erythema in a tooth, comprising:
    means for generating light of a first frequency;
    means for modulating said light of said first frequency to produce a modulated first light signal;
    means for generating light of a second frequency;
    means for modulating said light of said second frequency to produce a modulated second light signal, wherein said modulated second light signal is different from said modulated first light signal;
    means for transmitting said first and second light signals into the tooth;
    means for detecting shock waves induced in said tooth by said first and second light signals; and
    means for processing said detected shock waves induced in said tooth by said first and second light signals to measure erythema in said tooth.

2. A system according to claim 1, wherein said first frequency has a high absorption coefficient for blood.

3. A system according to claim 1, wherein said first frequency of light has a high absorption coefficient for oxygenated blood and said second frequency of light has a high absorption coefficient for deoxygenated blood.

4. A system according to claim 3, wherein said first and second frequencies of light have a high contrast in absorption with enamel and dentin.

5. A system according to claim 1, wherein said first frequency of light has a high absorption coefficient for blood and said second frequency of light has a low absorption coefficient for blood.

6. A system according to claim 1, wherein said first and second light signals are transmitted into said tooth simultaneously.

7. A system according to claim 1, wherein at least one modulation frequency used in said means for modulating said light of said first frequency is in a range between 500 to 50,000 KHz.

8. A system according to claim 1, further comprising:
    means for generating light of a third frequency;
    means for modulating said light of said third frequency to produce a modulated third light signal which is different from said modulated first and second light signals;
    said means for transmitting being effective for transmitting said third light signal into said tooth;
    said means for detecting being effective for detecting shock waves induced in said tooth by said transmitted light of said first, second, and third light signals; and
    said means for processing being effective for processing said detected shock waves induced in said tooth by said transmitted light of said first, second, and third light signals.

9. A system according to claim 8, wherein said third frequency has no specific absorption difference between oxygenated blood, deoxygenated blood, and at least one opaque area of said tooth.

10. A system according to claim 1, wherein said first frequency of light is in a near-infrared range.

11. A system according to claim 1, further comprising means for displaying a measure of erythema in said tooth.

12. A system according to claim 1, wherein said light is polarized.

13. A system according to claim 1, wherein said processing means includes a database containing data corresponding to a healthy tooth.

14. A system for measuring erythema in a tooth, comprising:
    means for generating light of a first frequency;
    transmitting means for transmitting said light of said first frequency into the tooth;
    detecting means for detecting shock waves induced in said tooth by said transmitted light of said first frequency;
    processing means for processing said detected shock waves induced by said transmitted light of said first frequency;
    means for generating light of a second frequency;
    said means for transmitting being effective for transmitting said light of said second frequency into said tooth;

said means for detecting being effective for detecting shock waves induced in said tooth by said transmitted light of said second frequency; and said means for processing being effective for processing said detected shock waves induced in said tooth by said transmitted light of said first and second frequency to measure erythema in said tooth;

wherein said first and second frequencies of light are transmitted into said tooth sequentially.

15. A system for measuring erythema in a tooth, comprising:
   a first generator for generating light of a first frequency;
   a probe which transmits said light of said first frequency into the tooth;
   a fiberoptic Fabry-Perot ultrasound sensor which detects shock waves induced in said tooth by said transmitted light of said first frequency; and
   a processor which processes said detected shock waves induced by said transmitted light of said first frequency to measure erythema in said tooth.

16. A system according to claim 15, wherein said probe includes a fiberoptic delivery portion surrounded by said ultrasound sensor.

17. A system according to claim 15, further comprising a second ultrasound sensor for sensing said shock waves.

18. A system for measuring erythema in a tooth, comprising:
   a first generator for generating light of a first frequency;
   a probe which transmits said light of said first frequency into the tooth;
   a detector which detects shock waves induced in said tooth by said transmitted light of said first frequency;
   a processor which processes said detected shock waves induced by said transmitted light of said first frequency;
   a second generator for generating light of a second frequency;
   a first modulator for modulating said light of said first frequency with a first pulse frequency;
   a second modulator for modulating said light of said second frequency with a second pulse frequency;
   wherein said probe transmits said modulated light of said first and second frequencies into said tooth;
   said detector detects shock waves induced in said tooth by said transmitted modulated light of said first and second frequencies; and
   said processor processes said detected shock waves induced by said transmitted modulated light of said first and second frequencies to measure erythema in said tooth.

19. A system according to claim 18, wherein said first frequency has a high absorption coefficient for oxygenated blood and said second frequency has a high absorption coefficient for deoxygenated blood.

20. A system according to claim 19, wherein said first and second frequencies have a high contrast in absorption with enamel and dentin.

21. A system according to claim 18, wherein said first frequency has a high absorption coefficient for blood and said second frequency has a low absorption coefficient for blood.

22. A system according to claim 18, wherein said first and second light signals are transmitted into said tooth simultaneously.

23. A system according to claim 18, wherein said first and second pulse frequencies are in a range between 500 to 50,000 KHz.

24. A system according to claim 18, further comprising:
   a third generator for generating light of a third frequency;
   a third modulator for modulating said light of said third frequency with a third pulse frequency;
   wherein said probe transmits said modulated light of said first, second, and third frequencies into said tooth;
   said detector detects shock waves induced in said tooth by said transmitted light of said first, second, and third frequencies; and
   said processor processes said detected shock waves induced in said tooth by said transmitted light of said first, second, and third light frequencies.

25. A system according to claim 24, wherein said third frequency has no specific absorption difference between oxygenated blood, deoxygenated blood, and at least one opaque area of said tooth.

26. A system for measuring erythema in a tooth, comprising:
   a first generator for generating light of a first frequency;
   a probe which transmits said light of said first frequency into the tooth;
   a detector which detects shock waves induced in said tooth by said transmitted light of said first frequency;
   a processor which processes said detected shock waves induced by said transmitted light of said first frequency;
   a generator for generating light of a second frequency;
   wherein said probe transmits said modulated light of said first and second frequencies into said tooth;
   said detector detects shock waves induced in said tooth by said transmitted light of said first and second frequencies; and
   said processor processes said detected shock waves induced by said transmitted light of said first and second frequencies to measure erythema in said tooth;
   wherein said first and second frequencies of light are transmitted into said tooth sequentially.

27. A system according to claim 26, wherein said first frequency of light is in a near-infrared range.

28. A system according to claim 26, further comprising a display for displaying a measure of erythema in said tooth.

29. A system according to claim 26, wherein said light is polarized.

30. A system according to claim 26, wherein said processor interacts with a database containing data corresponding to a healthy tooth.

31. A method for measuring erythema in a tooth, comprising the steps of:
   generating light of a first frequency;
   transmitting said light of said first frequency into the tooth;
   detecting shock waves induced in said tooth by said transmitted light of said first frequency; and
   processing said detected shock waves induced by said transmitted light of said first frequency to measure erythema in said tooth.

32. A method according to claim 31, wherein said first frequency has a high absorption coefficient for blood.

33. A method according to claim 31, further comprising the steps of:
   generating light of a second frequency;
   modulating said light of said first frequency to produce a modulated first light signal;
   modulating said light of said second frequency to produce a modulated second light signal, wherein said modulated second light signal is different from said modulated first light signal;
   transmitting said first and second light signals into said tooth;
   detecting shock waves induced in said tooth by said transmitted first and second light signals; and
   processing said detected shock waves induced by said transmitted light of said first and second light signals.

34. A method according to claim 33, wherein said first frequency has a high absorption coefficient for oxygenated blood and said second frequency has a high absorption coefficient for deoxygenated blood.

35. A method according to claim 34, wherein said first and second frequencies have a high contrast in absorption with enamel and dentin.

36. A method according to claim 33, wherein said first frequency has a high absorption coefficient for blood and said second frequency has a low absorption coefficient for blood.

37. A method according to claim 33, wherein said first and second light signals are transmitted into said tooth simultaneously.

38. A method according to claim 33, wherein at least one modulation frequency used in said steps of modulating is in a range between 500 to 50,000 KHz.

39. A method according to claim 33, further comprising the steps of:
generating light of a third frequency;
modulating said light of said third frequency to produce a modulated third light signal, wherein said modulated third light signal is different from said modulated first and second light signals;
transmitting said first, second, and third light signals into said tooth;
detecting shock waves induced in said tooth by said transmitted first, second, and third light signals; and
processing said detected shock waves induced by said transmitted light of said first, second, and third light signals.

40. A method according to claim 39, wherein said third frequency has no specific absorption difference between oxygenated blood, deoxygenated blood, and at least one opaque area of said tooth.

41. A method according to claim 31, further comprising the steps of:
generating light of a second frequency;
transmitting said light of said first and second frequencies sequentially into said tooth;
detecting shock waves induced in said tooth by said transmitted light of said first and second frequencies; and
processing said detected shock waves induced by said transmitted light of said first and second frequencies to measure said erythema in said tooth.

42. A method according to claim 31, wherein said first frequency of light is in a near-infrared range.

43. A method according to claim 31, further comprising the step of displaying a measure of erythema in said tooth.

44. A method according to claim 31, wherein said light is polarized.

45. A method according to claim 31, wherein said step of processing includes interacting with a database containing data corresponding to a healthy tooth.

* * * * *